US008781195B2

(12) United States Patent
Martinez-Möller et al.

(10) Patent No.: US 8,781,195 B2
(45) Date of Patent: Jul. 15, 2014

(54) METHOD FOR RECORDING AND PROCESSING MEASUREMENT DATA FROM A HYBRID IMAGING DEVICE AND HYBRID IMAGING DEVICE

(75) Inventors: Axel Martinez-Möller, München (DE); Stephan Nekolla, Esting (DE)

(73) Assignee: Siemens Aktiengesellschaft, Munich (DE)

( * ) Notice: Subject to any disclaimer, the term of this patent is extended or adjusted under 35 U.S.C. 154(b) by 423 days.

(21) Appl. No.: 12/822,234

(22) Filed: Jun. 24, 2010

(65) Prior Publication Data

US 2010/0329531 A1   Dec. 30, 2010

(30) Foreign Application Priority Data

Jun. 26, 2009   (DE) .......................... 10 2009 030 722

(51) Int. Cl.
*G06K 9/00*   (2006.01)
(52) U.S. Cl.
USPC ......................................................... 382/131
(58) Field of Classification Search
CPC .... G01R 33/481; A61B 6/037; A61B 6/5247; A61B 5/055; G06T 7/0012; G06T 2207/10072
USPC .............................. 382/131, 128; 250/363.04
See application file for complete search history.

(56) References Cited

U.S. PATENT DOCUMENTS 6,927,406 B2 *   8/2005   Zyromski ................... 250/496.1
7,286,867 B2 *   10/2007   Schlyer et al. ................ 600/407
7,312,610 B2 *   12/2007   Harder .......................... 324/307

(Continued)

FOREIGN PATENT DOCUMENTS

CN           1891149 A      1/2007
DE      102008004469 A1     7/2009

OTHER PUBLICATIONS

Dahlbom et al, Implementation of True Continuous 2D/3D Whole Body PET Scanning, Nuclear Science Symposium Conference Record, 2000 IEEE, vol. 3, pp. 17/13-17/17.*

(Continued)

*Primary Examiner* — John Pauls
*Assistant Examiner* — Jonathan Durant
(74) *Attorney, Agent, or Firm* — Harness, Dickey & Pierce, P.L.C.

(57) ABSTRACT

A method is disclosed for recording and processing measurement data from a hybrid imaging device including a first partial device for a first imaging modality and a second partial device for emission tomography. In at least one embodiment, the method includes: performance of measurement data recording with the first partial device, wherein successive different table positions are approached during the measurement data recording; recording of emission tomography measurement data with the second partial device during the performance of the measurement data recording with the first partial device at the different table positions; assignment of the recorded emission tomography measurement data to the different table positions; changing of the emission tomography measurement data assigned to different table positions with respect to the data volume in such a way that the recording times corresponding to the changed data volumes are matched to each other at different table positions; and reconstruction of an emission tomography image from the changed emission tomography measurement data. At least one embodiment of the invention further relates to a hybrid imaging device designed to perform the method.

14 Claims, 4 Drawing Sheets

(56) References Cited

U.S. PATENT DOCUMENTS

| | | | |
|---|---|---|---|
| 2003/0161521 A1* | 8/2003 | Newport et al. | 382/131 |
| 2006/0052685 A1* | 3/2006 | Cho et al. | 600/407 |
| 2007/0173716 A1* | 7/2007 | Mayer et al. | 600/410 |
| 2007/0242069 A1* | 10/2007 | Matsue et al. | 345/428 |
| 2008/0135756 A1 | 6/2008 | Kaga et al. | |
| 2008/0135769 A1* | 6/2008 | Rosen | 250/363.09 |
| 2008/0164875 A1* | 7/2008 | Haworth et al. | 324/318 |
| 2008/0170769 A1* | 7/2008 | Assmann | 382/128 |

OTHER PUBLICATIONS

Wilson JM, Turkington TG. Development of a PET protocol to equalize noise for PET/CT leg acquisitions. Paper presented at: IEEE Nuclear Science Symposium Conference Record, 2007.*

Carney JPJ, Watson CC, Townsend DW. Optimization of the relative acquisition duration for PET/CT imaging in oncology. Paper presented at: IEEE Nuclear Science Symposium Conference Record, 2004.*

Magnus Dahlbom et al.: "Methods for Improving Image Quality in Whole Body PET Scanning"; IEEE Transactions on Nuclear Science, vol. 39, No. 4, 1992, p. 1079-1083; Others; 1992; US.

Keiichi Matsumoto et al.: "Performance Characteristics of a New 3-Dimensional Continuous-Emission and Spiral-Transmission High-Sensitivity and High-Resolution PET Camera Evaluated with the NEMA NU 2-2001 Standard"; Performance of Large-Solid-Angle PET, p. 83-90, Journal Nucl. Med.2006; Others; 2006.

Z. Burbar et al.: "Continuous Bed Motion Data Processing for a High Resolution LSO PET/CT Scanner"; IEEE 2005, p. 2046-2048; vol. 4, Nuclear Science Symposium Conference Record, Oct. 23-29, 2005; Others; 2005; US.

D. Brasse et al.: "Continuous bed motion acquisition on an whole body combined PET/CT system"; 2003 IEEE, p. 951-955, Medical Imaging; Others; 2003; US.

Magnus Dahlborn et al.: "Implementation of True Continuous 2D/3D Whole Body PET Scanning", Medical Imaging conference, 2001 IEEE, p. 13-17; Others; 2001; US.

* cited by examiner

METHOD FOR RECORDING AND PROCESSING MEASUREMENT DATA FROM A HYBRID IMAGING DEVICE AND HYBRID IMAGING DEVICE

PRIORITY STATEMENT

The present application hereby claims priority under 35 U.S.C. §119 on German patent application number DE 10 2009 030 722.2 filed Jun. 26, 2009, the entire contents of which are hereby incorporated herein by reference.

FIELD

At least one embodiment of the invention generally relates to a method for recording and processing measurement data with a hybrid imaging device, which, in addition to a first imaging modality, is also able to perform and prepare emission tomography. At least one embodiment of the invention also generally relates to a hybrid imaging device. Hybrid imaging devices of this kind are, for example [known] as combined MR-PET systems (MR=magnetic resonance and PET=positron emission tomography) or as combined MR-SPECT systems (SPECT="Single Photon Emission Tomography).

BACKGROUND

Combined MR-PET systems or CT-PET systems are known in which it is possible to record both MR or CT measurement data and emission tomography measurement data in the same hybrid system. The first imaging modality (MR or CT) is able to depict the examination volume to be displayed in a first image, which mainly shows the anatomical relationships in the object to be examined. The second imaging modality (in this case PET) can be used to generate a further image. This mainly shows the distribution of a radioactive substance in the body and is hence able to depict biochemical and physiological functions (functional imaging).

The parallel creation of an image with two different modalities enables an improved evaluation of the state of the object to be examined.

During an examination, the object to be examined or the patient are often moved to different table positions to enable different regions of the patient to be depicted. With PET-CT imaging, a recording schedule is known with which the PET measurement data is recorded successively at different table positions with a predetermined recording time for each table position (so-called "step and shoot" mode). The CT measurement data are then recorded either before or after the performance of the PET measurement data recording.

SUMMARY

In at least one embodiment of the invention, a method is disclosed for recording and processing measurement data with a hybrid imaging device, which permits a short measurement data recording time and improved quality and conformity of the recorded data. In at least one embodiment of the invention discloses a hybrid imaging device with which a method of this kind can be performed.

The inventive method of at least one embodiment for recording and processing measurement data from a hybrid imaging device comprising a first partial device for a first imaging modality and a second partial device for emission tomography comprises:

performance of the measurement data recording with the first partial device, wherein, during the measurement data recording, successive different table positions are approached, recording of emission tomography measurement data with the second partial device during the performance of the measurement data recording with the first partial device at the different table positions, assignment of the recorded emission tomography measurement data to the different table positions, changing of the emission tomography measurement data assigned to different table positions with respect to the recorded data volume in such a way that the recording times corresponding to the changed data volumes are harmonized to each other at different table positions, reconstruction of an emission tomography image from the changed emission tomography measurement data.

At least one embodiment of the invention is based on the idea that, for the recording of the measurement data with the first imaging modality, during the recording process, it is often necessary to approach different table positions which are maintained for different times since, with the first imaging modality, different lengths of time are required for recording the measurement data for the different regions of the object to be examined. For example, the recording of MR measurement data for a leg may require less time than the recording of MR measurement data for an abdomen.

However, it was recognized that, during the performance of the first imaging modality, this time can also be advantageously used to record emission tomography measurement data. However, it has been found that a parallel recording of the emission tomography measurement data on its own is not sufficient to obtain an emission tomography image of the required quality. This is due to the fact that the different table positions and the times for which the different table positions are maintained are substantially matched to the first imaging modality.

Consequently, it is proposed for the further processing of the emission tomography measurement data that the recorded emission tomography measurement data be analyzed with respect to the recorded data volume and/or with respect to the recording times at the different table positions. During the emission tomography, the recording time of the emission tomography measurement data is correlated with the recorded data volume. Hereby, the emission tomography measurement data can be recorded with a value characterizing the table position so that the emission tomography measurement data can subsequently be assigned to the table positions.

In this way, it is possible, for example, to determine whether at individual or all table positions, a sufficient amount or sufficient length of emission tomography measurement data have been recorded in order to achieve a minimum quality standard for the respective emission tomography reconstruction at every table position.

For example, it is possible to determine whether emission tomography measurement data have been recorded in greater amounts or for longer times at individual or several table positions than at other table positions. The result of this would be that an emission tomography reconstruction would have a different image quality in some image sections than in other image sections. This can be particularly noticeable if a whole emission tomography is to be reconstructed from the individual emission tomography sections, since then the whole emission tomography would be of non-uniform quality.

Overall, therefore, the recorded emission tomography measurement data are analyzed with respect to the recorded data volume or with respect to the recording times and changed so that different recording times are harmonized. This harmonization can be performed with respect to a quality criterion during the reconstruction of the respective emission tomography assigned to one of the table positions so that, for example, the individual emission tomography image sections have a homogeneous quality.

This is achieved in that the emission tomography data assigned to the different table positions are changed and to be precise with respect to their data volume. Hereby, the change takes place in such a way that the recording times, which each correspond to the data volume at the different table positions, are harmonized to each other so that the data acquisition time at the different table positions is substantially the same or comparable. In this way, it is possible to reconstruct emission tomography sections at the different table positions with the same image quality. The reconstruction of a whole emission tomography from the individual emission tomographies enables the achievement of a more homogeneous image quality.

Overall, the recording schedule results in a shorter recording time for both imaging modalities since emission tomography measurement data are already obtained during the recording of the measurement data for the first partial device. Artifacts or a lack of conformity between the emission tomography measurement data and the measurement data from the first partial device, which can occur during sequential recording of the two imaging modalities due to patient movements and could consequently represent incongruence between the two imaging modalities, are reduced or are less likely to occur. In addition, a lower recording time entails lower operating costs and lower wear of the hybrid imaging device when producing a combined image with the two imaging modalities.

The table positions, which have to be successively approached with the first imaging modality, do not necessarily also have to be located next to each other. For example, the brain of a patient can be positioned in the FoV ("field of view") of the first imaging modality at a first table position, and the hip region at a second table position, if these regions are to be targeted for examination. It is not compulsory for measurement data to be recorded at intermediate stations, i.e. the neck, thorax and abdomen.

The emission tomography measurement data can be changed in that, at least one of the different table positions, a reduction of the recorded emission tomography data assigned to this table position takes place in that a part of this recorded emission tomography measurement data is discarded. This can for example be advantageous if a comparable minimum amount of emission tomography measurement data has already been recorded at each table position and if significantly more emission tomography measurement data were recorded at one of the table positions than at the other table positions. In this case, it can be advantageous to discard measurement data at this one table position. No additional data acquisition time is required.

However, emission tomography measurement data can also be changed in that, at least one of the table positions, there is an increase in the recorded emission tomography data assigned to this table position, in that further emission tomography measurement data are additionally recorded at this table position. This can, for example, be advantageous if it is identified, that at this one table position, the dwell time with the first imaging modality was too short to record the necessary minimum amount of emission tomography measurement data for the desired quality on reconstruction. In this case, this table position can be additionally approached in order additionally to perform a supplementary recording of the further measurement data.

In at least one embodiment, the two methods can also be combined, i.e. at some table positions, a supplementary recording can be performed while at other table positions, measurement data can be discarded so that overall the recording time at each different table position is adjusted in order to obtain the same or harmonized recording time.

In an advantageous variant, the additional recording of the emission tomography measurement data is performed when the recording of the measurement data with the first partial device is completed.

Alternatively and/or additionally, the additional recording of the emission tomography measurement data can be performed while the measurement data recording with the first partial device is being performed. In the latter case, for example, the measurement data recording with the first partial device can comprise a first part measurement data recording and a temporally subsequent second part measurement data recording with a waiting time in between. The waiting time can, for example, be due to the fact that the second part measurement data recording required a certain preparation time. In this case, the additional recording of the emission tomography measurement data can be performed during the waiting time hence resulting in optimum utilization of the hybrid imaging device.

In one variant of at least one embodiment of the method, a minimum recording time can be determined. This minimum recording time is then based on the change to the emission tomography measurement data with respect to the data volume, wherein, at each table position, the recording times corresponding to the changed data volumes should be greater than the minimum recording time. The minimum recording time can, for example, also depend on the geometry of the object to be examined.

In an advantageous variant, the minimum recording time can be determined separately for different table positions depending upon the attenuation of emission tomography photons that occurs at the respective table positions. With this embodiment, the method can be matched to the anatomical circumstances of the object to be examined. For example, at one table position in which the abdomen is positioned for the imaging, a longer minimum recording time may be determined, since there is greater attenuation of the photons emitted from the abdomen compared, for example, to table positions in which only the lower leg is positioned for imaging.

The emission tomography can for example be positron emission tomography or single photon emission computed tomography.

The hybrid imaging device according to at least one embodiment of the invention has a first partial device for a first imaging modality, a second partial device for emission tomography and a control device for controlling the first and the second partial device, wherein the control device is embodied for performing a method according to one embodiment of the invention.

Hereby, the control device is usually divided between one or more computer units. For example, one computer unit can take over the control of the first partial device for recording the measurement data, another computer unit the control of the second partial device for recording the measurement data, and a further computer unit the evaluation and processing of the recorded data right up to the reconstruction of an image. The computer unit, the other computer unit and/or an additional computer unit can also be responsible for the control of the patient table in order to enable it to be controlled and positioned suitably for the measurement data recording. In particular, there can be a reconstruction of a hybrid image, which depicts the object to be examined with both the first imaging modality and with the emission tomography.

BRIEF DESCRIPTION OF THE DRAWINGS

Embodiments of the invention will be explained in more detail with reference to the following drawings but is not restricted thereto. The drawings show.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
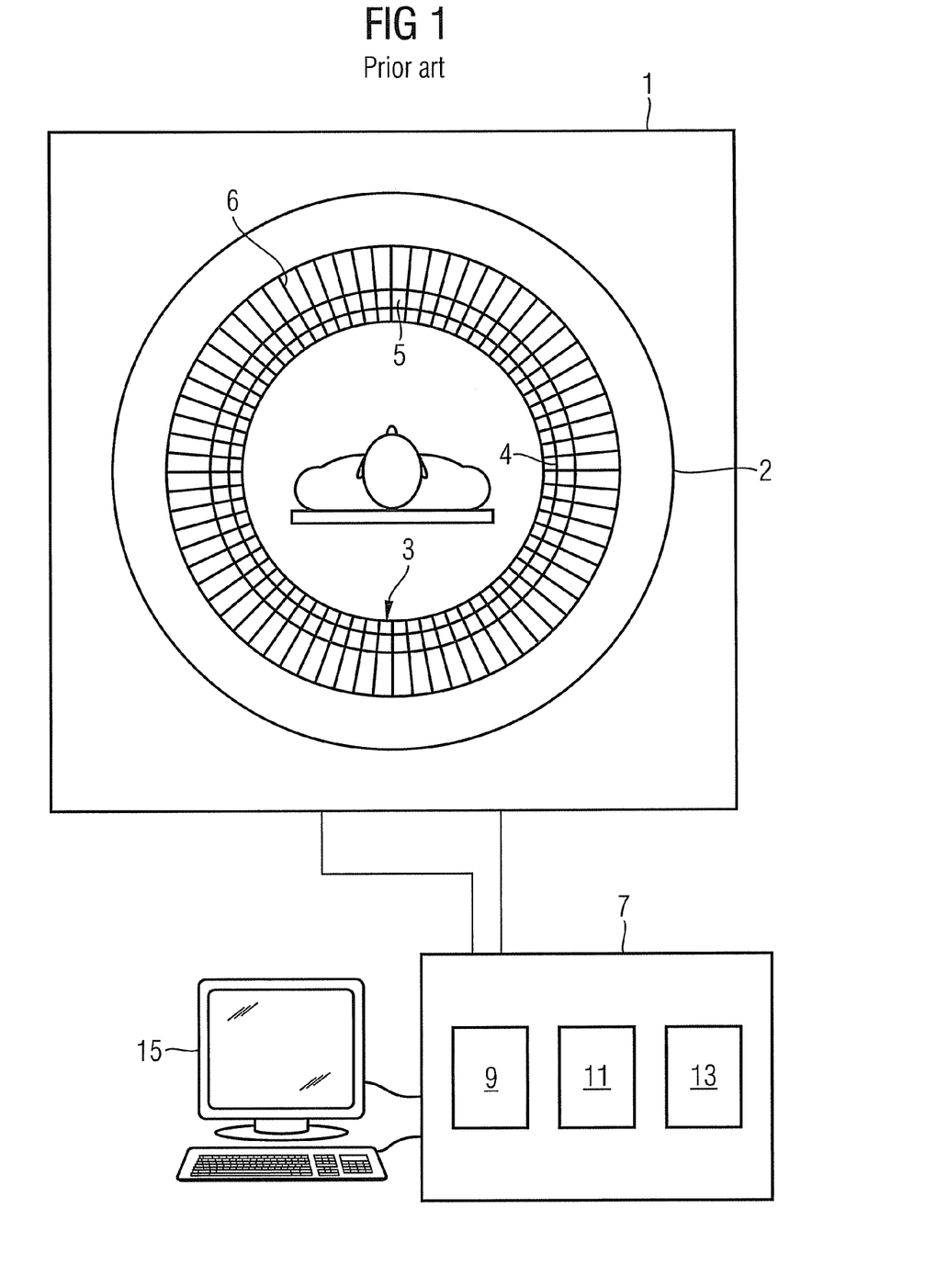
FIG. 1 a schematic representation of a hybrid imaging device embodied as an MR-PET device, FIG. 2 a schematic representation of the data volumes recorded at different table positions, FIG. 3 a representation of the PET data volumes recorded at different table positions, FIG. 4 a representation of the PET data volumes after harmonization to a threshold value, FIG. 5 a representation of the PET data volumes after harmonization to a variable threshold value, FIG. 6 a schematic representation of method steps performed in one embodiment of the method according to the invention.

FIG. 1 shows a known combined MR-PET device 1, which is used with a preferred embodiment of the invention. A combined MR-PET device has the advantage that both MR and PET data can be obtained isocentrically. In addition, the measurement data can be recorded simultaneously.

In principle, parallel recordings can also be performed if the MR-PET device does not have an isocentric design. In this case, it is possible to perform simultaneous measurement data recordings with each of the two modalities for different regions.

The MR-PET device 1 comprises a known tubular MR unit 2. The MR unit 2 is only indicated schematically and defines a longitudinal direction z extending orthogonally to the plane of the drawing in FIG. 1.

As shown in FIG. 1, several PET detection units 3 facing each other arranged in pairs about the longitudinal direction z are arranged coaxially within the MR unit 2. The PET detection units 3 preferably consist of an APD photodiode array 5 with an upstream array of LSO crystals 4 and an electrical amplifying circuit (AMP) 6. However, the invention is not restricted to the PET detection units 3 with the APD-photodiode array 5 and the upstream array of LSO crystals 4. It is equally possible to use other types of photodiodes, crystals and appliances for detection.

During an MR and/or PET examination, a patient to be examined with a patient table, table for short, is moved successively to different positions in order in each case to move the section to be examined into the examination region (field of view) of the MR unit 2 or the PET unit.

The MR-PET device 1 is controlled by a control device 7. The control device 7 can, for example, comprise a first partial device 9 to control the MR unit and a second partial device 11 to control the PET unit for the performance of the measurement data recording. The first partial device 9 and/or the second partial device 11 can also control and suitably position the patient table. In addition, the control device 7 can comprise an evaluation computer 13, which is connected to the partial devices 9, 11, analyzes the recorded measurement data and can create a hybrid image 15 of the object to be examined. The hybrid image 15 can be displayed to a user or stored in a storage unit. The components of the control device 7 are interconnected.

A device of this kind is known.

The control device 7 with its units 9, 11, 13 is developed in such a way that the new method described below with reference to FIG. 2 to FIG. 5 can be performed.

Figure 2:
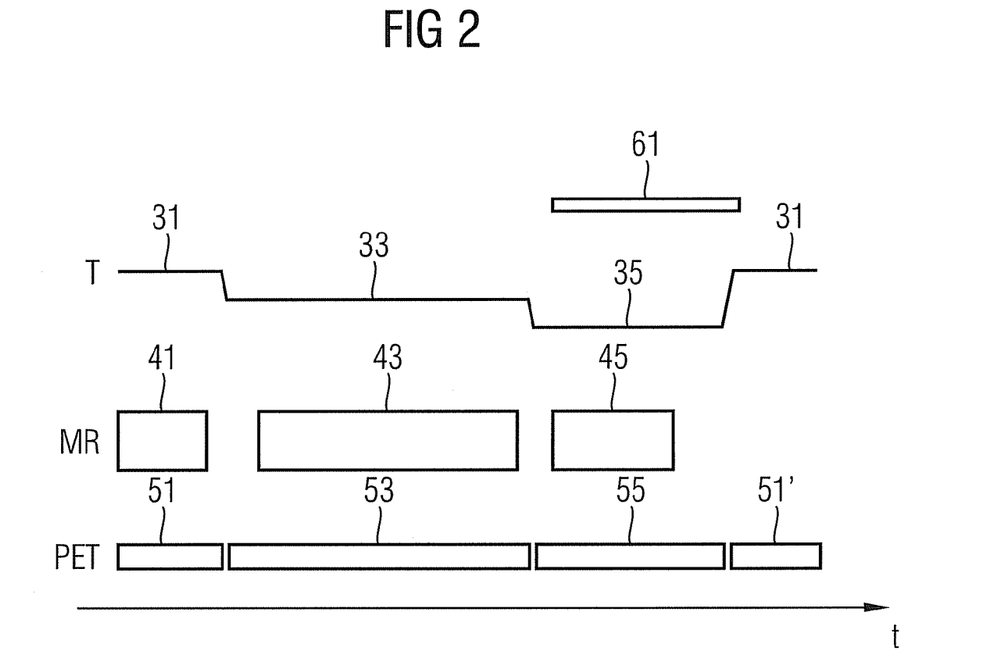

FIG. 2 show an examination process, plotted against the time t, depicting an embodiment of the method according to the invention.

The upper part T of the image shows three different table positions 31, 33, 35, which are approached for the performance of the MR examination. These table positions can, for example, correspond to an examination of the brain, the abdomen and the legs.

The middle part MR of the image shows the recording of the MR measurement data. At the first table position 31, the first MR measurement data 41 for the brain are recorded, at the second table position 33 the second MR measurement data 43 for the abdomen and [at] the third table position 35 the third MR measurement data 45 for the legs.

Between each of the individual MR measurement data recordings, there is a certain waiting time. During this waiting time, preparation for the examination of the next region takes place and the table is moved to the respective position. The recording of the MR measurement data 41, 43, 45 requires different times at the individual table positions 31, 33, 35.

The lower part PET of the image shows the recording of the PET measurement data 51, 51', 53, 55. It is evident that the PET measurement data are recorded partially in parallel to the MR measurement data 41, 43, 45. Hereby, the recording takes place in the background in what is known as list-mode data format. The table positions 31, 33, 35 are recorded simultaneously so that, during the course of the further processing, it is possible to assign the PET measurement data 51, 51', 53, 55 to the table position 31, 33, 35 at which they are respectively recorded.

With emission tomography, list-mode data format means the raw data, that is the events detected by the detectors which are recorded together with a time stamp. This data format requires a comparatively large amount of storage space. Therefore, with emission tomography, it is usual to record the measurement data in a pre-processed format which overall requires less storage space, but which is sufficient for conventional emission tomography reconstruction.

However, besides the drawback mentioned, the list-mode-data format has the advantage that it permits greater flexibility for image reconstruction since the data can subsequently be modified and processed and is therefore used with embodiments of the invention.

The recording of the PET measurement data 51, 51', 53, 55 is performed at the table positions 31, 33, 35 even when no MR measurement data 41, 43, 45 are recorded, during the waiting time for example. It is only during the movement of the patient table that the recording of the PET measurement data 51, 51', 53, 55 is interrupted. If there is a longer waiting time, the table can also be moved specifically for the recording of PET measurement data to a position at which it is still necessary to record or to supplement PET measurement data (not shown here).

Due to the different lengths of the dwell times at the table positions, at some table positions, data were recorded in a smaller amount or for a shorter time than at other table positions.

However, it was determined in advance that to achieve a minimum degree of quality with a reconstructed PET image at each table position, it is necessary to record a minimum amount of data, symbolized by the bar 61, which represents the minimum recording duration.

The example shows that, at the first table position 31 during the recording of the first MR measurement data 41, first PET measurement data 51 are recorded, the data volume of which is too low compared to the required minimum amount or minimum acquisition time (bar 61).

At the second table position 33, on the other hand, a sufficient amount of second PET measurement data 53 are recorded.

At the third table position 35, immediately after the completion of the third MR measurement data 45, once again an insufficient amount of third PET measurement data 55 are recorded. Therefore, immediately after the completion of the recording of the third MR measurement data 45, the patient remains at the third table position 35 and the recording of the third PET measurement data 55 is completed until a minimum amount 61 of PET measurement data for the third table position 35 has been achieved.

Then, the table is moved back to the first table position 31 in order also to record further first PET measurement data 51' for the first table position 31, once again until the required minimum amount of PET measurement data 61 for the first table position 31 has been recorded.

Figure 3:
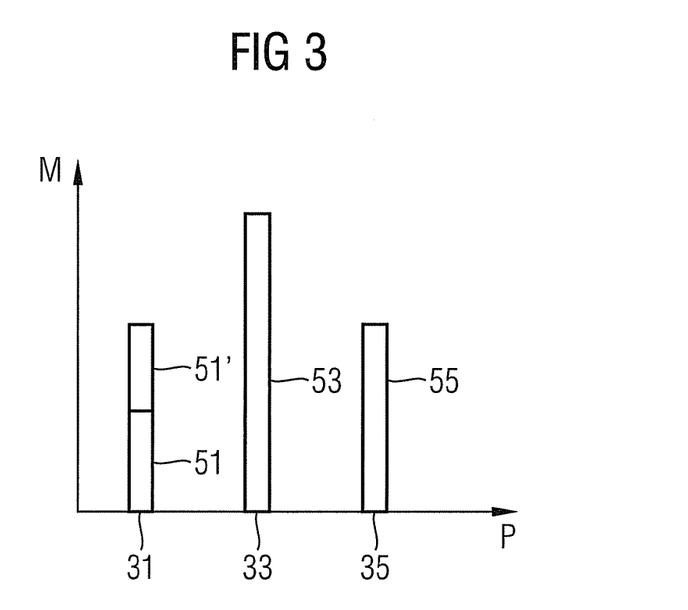

After the completion of the measurement data recording, the situation depicted in FIG. 3 for the PET measurement data prevails. The recorded data volume M is plotted against the table position P adopted there. The recorded PET measurement data 51, 51', 53, 55 are sorted and assigned to the individual table positions 31, 33, 35. The left column corresponds to the first table position 31, the middle column to the second table position 33 and the right column to the third table position 35.

Despite the additional recording of the further first PET measurement data 51' and the extended recording of the third PET measurement data 55 for the first and for the third table position 31, 35, there are still different amounts of PET measurement data with respect to the data volume/recording time, since substantially more second PET measurement data 53 were recorded at the second table position 33. If a whole PET image had been created from all the PET measurement data 51, 51', 53, 55, the quality of this image would be non-uniform in layers or stages, in particular layers of the abdomen would be depicted with a different quality than layers of the legs or the head. This can mislead a user tasked with evaluating the image.

Figure 4:
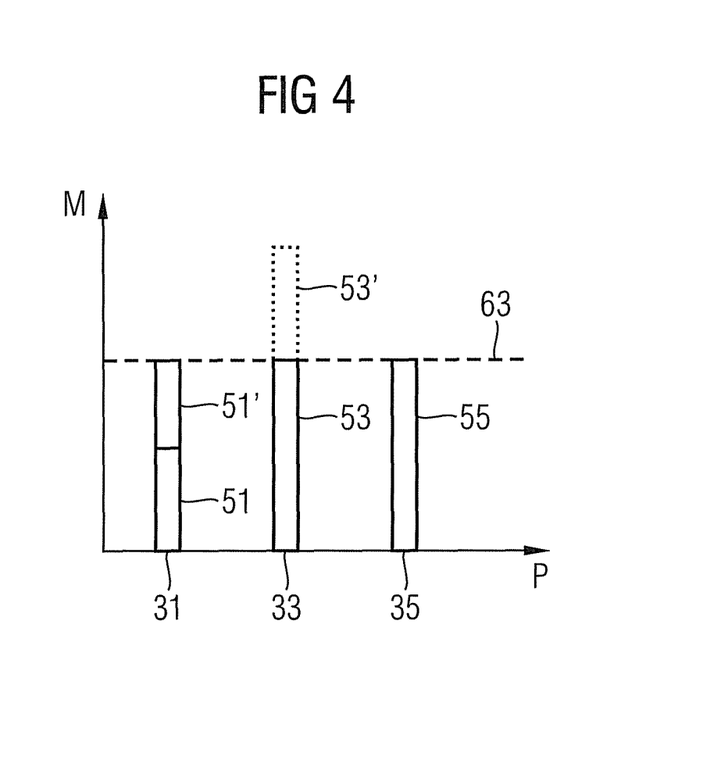

Therefore, during the further processing of the measurement data, a part 53' of the second PET measurement data 53 is discarded, as depicted in FIG. 4. Subsequently, it is possible to use the measurement data supplemented/corrected in such a way to create a whole PET image, which does not have the problem described.

Figure 5:
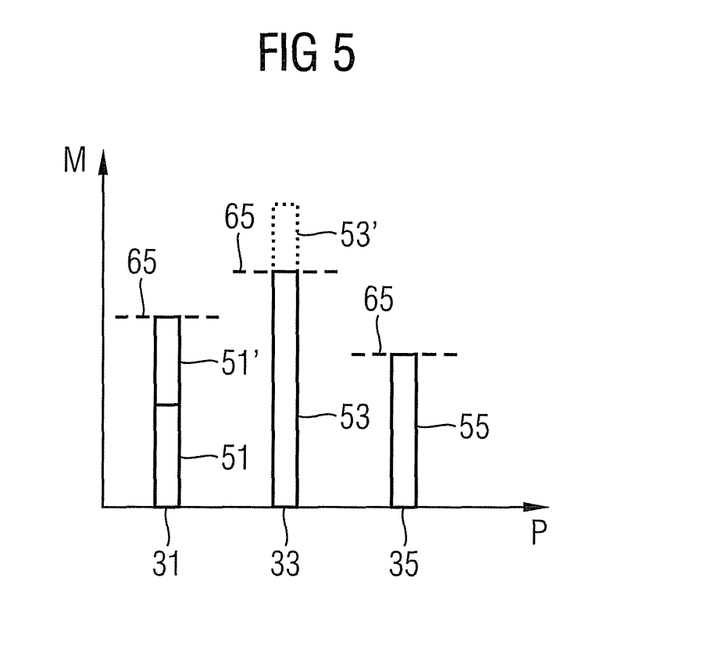

FIG. 5 shows a modification of the method depicted in FIG. 4. FIG. 4 shows the same threshold value 63 for each table position 31, 33, 35, corresponding to the bar 61. Therefore, this is based on the same minimum recording time as that used to determine whether there is any further PET measurement data recording or any rejection of PET measurement data.

FIG. 5. on the other hand, shows a variable threshold value 65, i.e. a minimum recording time, which differs from table position to table position. This variable threshold value 65 is determined by the expected attenuation of photons which occurs with emission tomography. The expected attenuation can, for example, be determined or estimated from the recorded MR measurement data or from the MR image data reconstructed therefrom.

For example, greater attenuation is to be expected for the photons formed in the abdomen than, for example, in the head region or in the leg region. For this reason, the minimum recording time for the abdomen is selected higher in order to obtain a data volume of PET measurement data for the reconstruction.

The method and variants thereof explained here are particularly advantageous if a tracer which is long-lived compared to a typical examination duration is used for the PET imaging, for example 18F-FDG (18F-fluorodesoxyglucose). If, due to the clinical application, it is necessary to use a short-lived tracer, a conventional recording schedule with sequential recording of first the PET measurement data and then the MR measurement data can be of advantage. The hybrid imaging device is therefore designed in such a way that a user can choose between a conventional recording schedule and a method according to at least one embodiment of the invention.

The example embodiments explained with reference to FIG. 3 to FIG. 5 have table positions which are in conformity for the first imaging modality and for the emission tomography. This is not a compulsory requirement.

The table positions, which are approached during the first imaging modality also do not have to be in full conformity with the table positions approached during emission tomography.

It can, for example, be the case that the MR device has a FoV of 20 cm. For the MR imaging, the patient can be positioned at a first table position with which a patient region of 0 cm to 20 cm can be measured and depicted. At a second position, a patient region of 30 cm to 50 cm is measured or depicted.

Hereby, after the completion of the measurement, it is possible to record additional PET measurement data which complete the region of 20 cm to 30 cm. To this end, after the completion of the MR measurements, the patient can be moved to a third table position (covering, for example, the region from 15 cm to 35 cm), at which additional PET measurement data are recorded.

Figure 6:
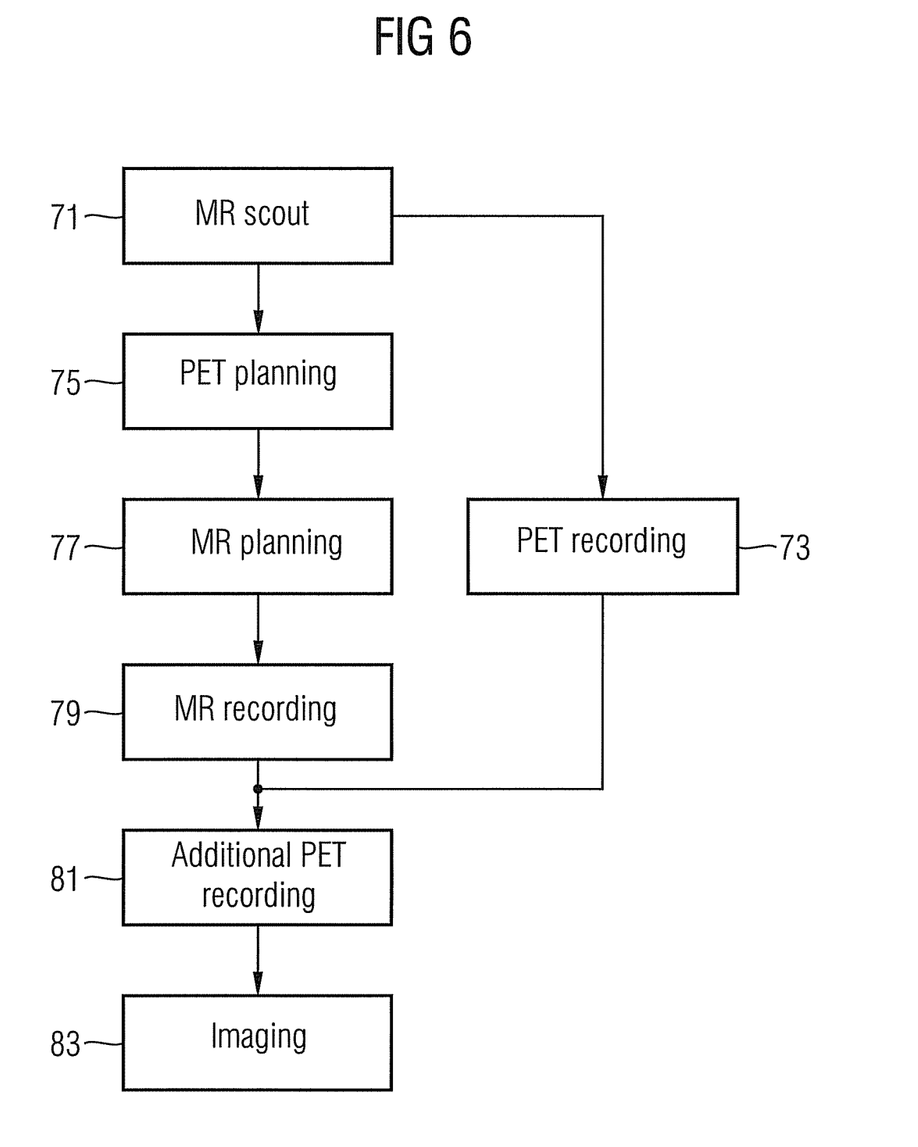

FIG. 6 is a schematic representation of method steps which can be performed with one embodiment of the method.

Firstly, an MR overview image (so-called scout image) is recorded (step 71). This MR overview image can be recorded with little time expenditure, for example within 20 s per table position. PET measurement data can be recorded in the background during this recording (step 73). The MR overview image is not used for diagnostic purposes. It is used to plan the following steps for the subsequent acquisition.

The MR overview image can also be used to perform an attenuation correction during the reconstruction of the PET image or to determine the minimum amount of PET measurement data to be recorded per FoV. To this end, however, it is also possible to record additional MR measurement data, in particular if the MR overview image was recorded with parameters which would not permit the determination of an attenuation correction from the MR overview image.

Subsequently, the FoVs for the PET measurements are determined from the MR overview image (step 75). PET measurement data which were already recorded during the MR overview image can already be assigned to the individual FoVs.

In a further step 77, the patient and disease-specific planning of the MR measurement is performed with reference to the MR overview image. No MR measurement data are recorded during this planning phase. However, even in this planning phase, which takes a certain amount of time, recording of PET measurement data takes place (step 73), the measurement data being recorded permanently in the background.

If desired, in this phase the patient or the patient table can already be moved to different positions in that the table positions at which PET measurement data are still missing or will be missing are determined.

This is followed by the recording of MR measurement data (step 79). Once again, during this recording of MR measurement data, PET measurement data continue to be recorded in parallel.

When the recording of the MR measurement data is complete, optionally further PET measurement data are recorded (step 81), and to be precise until sufficient PET measurement data are recorded for all FoVs, such as were defined in step 75.

After the end of the entire recording of measurement data, there is a further harmonization of the PET measurement data as was explained with reference to FIG. 3 to FIG. 5.

Individual MR or PET images and/or a hybrid image are reconstructed from the MR measurement data or from the PET measurement data (step 83).

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE NUMBERS

1 MR-PET device
2 MR unit
3 PET detection units
4 LSO crystals
5 APD photodiode array
6 Electrical amplifying circuit
7 Control device
9 First partial device
11 Second partial device
13 Evaluation computer
15 Hybrid image
31 First table position
33 Second table position
35 Third table position
41 First MR measurement data
43 Second MR measurement data
45 Third MR measurement data
51 First PET measurement data
53 Second PET measurement data
55 Third PET measurement data
51' Further first PET measurement data
53' Part of the second PET measurement data
61 Bar
63 Threshold value
65 Variable threshold value

What is claimed is:

1. A method for recording and processing measurement data from a hybrid imaging device including a first partial device for a first imaging modality and a second partial device for emission tomography, said method comprising:
   first performing measurement data recording with the first partial device, wherein successive different table positions associated with recording times, respectively, are approached during the measurement data recording;
   recording emission tomography measurement data with the second partial device during the performing of the measurement data recording with the first partial device at the different table positions;
   assigning the recorded emission tomography measurement data to data sets, each data set containing emission tomography measurement data recorded at one of the different table positions, a volume of emission tomography measurement data in each of the data sets being correlated to the recording time at the respective table position;
   determining, for each data set, at least one of a recording time at the respective table position and the volume of emission tomography measurement data in the data set;
   changing the volume of emission tomography measurement data in at least one of the data sets by at least one of increasing and reducing the volume of recorded emission tomography data in the at least one data set such that the recording times correlated to the volume of emission tomography measurement data in the data sets are greater than threshold recording times, respectively; and
   reconstructing an emission tomography image from the changed emission tomography measurement data.

2. The method as claimed in claim 1, wherein the changing includes reducing the recorded emission tomography-data assigned to at least one of the different table positions such that a part of the recorded emission tomography measurement data assigned to the at least one of the different table positions is discarded.

3. The method as claimed in claim 1, wherein the changing includes increasing the recorded emission tomography-data assigned to at least one of the different table positions such that an additional recording of emission tomography measurement data is performed at the at least one of the different table positions.

4. The method as claimed in claim 3, wherein the additional recording is performed after the first performing.

5. The method as claimed in claim 3, wherein the additional recording is performed during the first performing.

6. The method as claimed in claim 5, wherein the first performing includes a first part measurement data recording and a temporally subsequent second part measurement data recording between which there is a waiting time, wherein the additional recording of the emission tomography measurement data is performed during the waiting time.

7. The method as claimed in claim 1, wherein each threshold recording time is based on an attenuation of emission tomography photons that occurs at a corresponding different table position.

8. The method as claimed in claim 7, wherein the attenuation of the emission tomography photons that occurs is based on the measurement data recorded by the first partial device.

9. The method as claimed in claim 1, wherein the emission tomography measurement data are recorded in a list-mode-data format.

10. The method as claimed in claim 1, wherein the first partial device is a magnetic resonance device and the second partial device is a positron emission tomography appliance.

11. The method as claimed in claim 2, wherein the changing includes increasing the recorded emission tomography-data assigned to another of the different table positions such that an additional recording of emission tomography measurement data is performed at the another of the different table positions.

12. The method as claimed in claim 11, wherein the additional recording is performed after the first performing.

13. A hybrid imaging device, comprising:
a first partial device for a first imaging modality;
a second partial device for emission tomography; and
a control device to control the first and the second partial device for at least:
performing measurement data recording with the first partial device, wherein successive different table positions associated with recording times, respectively, are approached during the measurement data recording;
recording emission tomography measurement data with the second partial device during the performing of the measurement data recording with the first partial device at the different table positions;
assigning the recorded emission tomography measurement data to data sets, each data set containing emission tomography measurement data recorded at one of the different table positions, a volume of emission tomography measurement data in each of the data sets being correlated to a recording time at the respective table position;
determining, for each data set, at least one of a recording time at the respective table position and the volume of emission tomography measurement data in the data set;
changing the volume of emission tomography measurement data in at least one of the data sets by at least one of increasing and reducing the volume of recorded emission tomography data in the at least one data set such that the recording times correlated to the volume emission tomography measurement data in the data sets are greater than threshold recording times, respectively; and
reconstructing an emission tomography image from the changed emission tomography measurement data.

14. A non-transitory computer readable medium for recording and processing measurement data from a hybrid imaging device including a first partial device for a first imaging modality and a second partial device for emission tomography, the computer readable medium including program segments for, when executed on a computer device, causing the computer device to:
first perform measurement data recording with the first partial device, wherein successive different table positions associated with recording times, respectively, are approached during the measurement data recording;
record emission tomography measurement data with the second partial device during the performing of the measurement data recording with the first partial device at the different table positions;
assign the recorded emission tomography measurement data to data sets, each data set containing emission tomography measurement data recorded at one of the different table positions, a volume of emission tomography measurement data in each of the data sets being correlated to a recording time at the respective table position;
determine, for each data set, at least one of a recording time at the respective table position and the volume of emission tomography measurement data in the data set;
change the volume of emission tomography measurement data in at least one of the data sets by at least one of increasing and reducing the volume of recorded emission tomography data in the at least one data set such that the recording times correlated to the volume emission tomography measurement data in the data sets are greater than threshold recording times, respectively; and
reconstruct an emission tomography image from the changed emission tomography measurement data.

* * * * *